US006812246B2

(12) United States Patent
Snader et al.

(10) Patent No.: US 6,812,246 B2
(45) Date of Patent: Nov. 2, 2004

(54) AMINOFLAVONE COMPOUNDS, COMPOSITIONS, AND METHODS OF USE THEREOF

(75) Inventors: Kenneth M. Snader, Germantown, MD (US); B. Rao Vishnuvajjala, Rockville, MD (US); Tsutomu Akama, Sunnyvale, CA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/240,883

(22) PCT Filed: Apr. 6, 2001

(86) PCT No.: PCT/US01/11434

§ 371 (c)(1),
(2), (4) Date: Jun. 12, 2003

(87) PCT Pub. No.: WO02/081462

PCT Pub. Date: Oct. 17, 2002

(65) Prior Publication Data

US 2004/0019227 A1 Jan. 29, 2004

Related U.S. Application Data

(60) Provisional application No. 60/195,507, filed on Apr. 6, 2000.

(51) Int. Cl.[7] .............................................. A61K 31/35
(52) U.S. Cl. ....................................... 514/456; 549/403
(58) Field of Search ........................... 549/403; 514/456

(56) References Cited

FOREIGN PATENT DOCUMENTS

| EP | 0 556 720 A1 | 8/1993 |
|----|--------------|--------|
| EP | 0 638 566 A1 | 2/1995 |
| EP | 0 755 928 A1 | 1/1997 |

OTHER PUBLICATIONS

Phillips, L. R. et al, 'Identification of the principal circulating metabolite of a synthetic 5,4'–diaminoflavone (NSC 686288), an antitumor agent, in the rat' 133:68295 (2000).*
Akama et al., *J. Med. Chem.*, 41, 2056–2067 (1998).
Boyd et al., *Cytotoxic Anticancer Drugs: Models and Concepts for Drug Discovery and Development*, Valeriote et al., eds., Amsterdam: Kluwer Academic Pulbishers, 11–34 (1990).

Boyd, *Current Therapy in Oncology*, ed. Niederhuber, Philadelphia: B.C. Decker, Inc., 11–22 (1993).
Boyd et al., *Drug Dev. Res.*, 34, 91–109 (1995).
Boyd, *Anticancer Drug Development Guide: Preclinical Screening, Clinical Trials, and Approval*, ed., Teicher, B.A. Totowa, N.J.: Humana Press, Inc., 23–42 (1997).
Chabner and Collins, *Cancer Chemotherapy: Principles and Practice*, eds., J. B. Lippincott, Chapter 2 (1990).
Devita et al., *Cancer: Principles and Practice of Oncology Updates*, eds., Philadelphia: Lippincott, 1–12 (1990).
Grever and Chabner, *Cancer: Principles and Practice of Oncology*, 5[th Ed.], DeVita et al., eds, Philadelphia: Lippincott–Raven, 385–394 (1997).
Monks et al., *J. Natl. Cancer Inst.*, 83(11), 757–766 (1991).
Rubinstein et al., *J. Natl. Cancer Inst.*, 82(13), 1113–1118 (1990).
Skehan et al., *J. Natl. Cancer Inst.*, 82(13), 1107–1112 (1990).
Stinson et al., *Anticancer Res.*, 12, 1034–1035 (1992).
Weinstein et al., *Science*, 275, 343–349 (1997).
Wingard et al., *Human Pharmacology*, eds., St. Louis: Mosby–Year Book, Inc., 50–63 (1991).

* cited by examiner

*Primary Examiner*—Amelia A. Owens
(74) *Attorney, Agent, or Firm*—Leydig, Voit & Mayer, Ltd.

(57) ABSTRACT

The invention provides an aminoflavone having formula (I), wherein each of $R^1$ and $R^2$ is H, $COCH_2$—$R^7$, wherein $R^7$ is amino alkylamino, dialkylamino, or alkyl- or dialkylaminoalkyl, or an α-amino acid residue, provided that at least one of $R^1$ or $R^2$ is other than H, and $R^3$ is H, branched or straight-chain alkyl, hydroxyalkyl, alkanoyloxyalkyl, alkanoyloxy, alkoxy, or alkoxyalkyl, or pharmaceutically acceptable salts thereof. The present invention also provides a pharmaceutical composition comprising an aminoflavone as described above, and a method of inhibiting the growth of a tumor in a host by administering a tumor growth-inhibiting amount of an aminoflavone compound having the formula as described above.

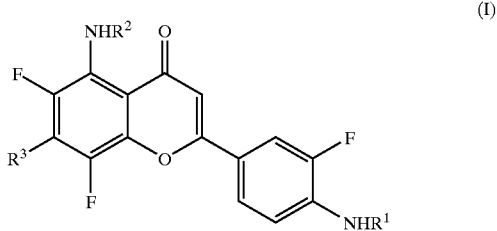

(I)

15 Claims, 5 Drawing Sheets

AMINOFLAVONE COMPOUNDS, COMPOSITIONS, AND METHODS OF USE THEREOF

CROSS-REFERENCE TO RELATED PATENT APPLICATIONS

This patent application is a national phase application of International Patent Application No. PCT/US01/11434, filed Apr. 6, 2001, which designates the U.S. and claims the benefit of U.S. Provisional Patent Application No. 60/195,507, filed Apr. 6, 2000.

TECHNICAL FIELD OF THE INVENTION

The present invention relates to novel 5-aminoflavone compounds, compositions, and methods of using these compounds as cytotoxic agents.

BACKGROUND OF THE INVENTION

Flavonoids, either natural or synthetic, have been recognized as exhibiting various biological activities. Such compounds, for example, may inhibit protein kinase C, aromatase, topoisomerase, or cyclin-dependent kinase activity or may exhibit antimitotic activity. In particular, 5,4'-diaminoflavones reportedly exhibit cytotoxicity against, for example, the human breast cancer cell line MCF-7. See Akama et al., *J. Med. Chem.*, 41, 2056–2067 (1998).

The mechanism of action and the target molecule of the 5,4'-diaminoflavone compounds remain largely unknown. Experiments incorporating various substituent groups at the 6, 7, 8, and 3'-positions on the flavone ring yielded some speculation as to the structure-activity relationship of the substituents, particularly at the 7-position of 5,4'-diamino-6,8,3'-trifluoroflavone. Although the real role of the various substituent groups remains unclear, it was demonstrated that certain physical properties of the parent flavone compound, such as solubility, could be improved by the presence of some, but not all, substituent groups at the 7-position. Some of the 7-substituted compounds also demonstrated cytotoxicity against human breast cancer cells. See Akama et al., *J. Med. Chem.*, at 2061–62.

Despite the cytotoxicity of 5,4'-diamino-6,8,3'-trifluoroflavone against certain human cancer cells, the compound possesses poor solubility in organic solvents and hardly solubilizes in water. In fact, solubility data of 5,4'-diamino-6,8,3'-trifluoroflavone were found to be less than 0.2 $\mu$g/mL in water and 1.2 mg/mL in ethanol. See Akama et al., *J. Med. Chem.*, at 2067.

Water solubility provides a critical advantage for a pharmaceutical compound, especially with respect to the formulation of the drug and oral absorption after administration. In most cases, the site of drug action is located in a region that is separated from the site of drug administration by a membrane. Drugs that are administered orally, intramuscularly, or subcutaneously must cross membranes to be absorbed and to enter the systemic circulation. Even drugs administered by intravenous injection must cross capillary membranes in order to leave the systemic circulation and enter intracellular and extracellular sites of action. See *Human Pharmacology*, Wingard et al., eds., St. Louis: Mosby-Year Book, Inc., 1991, pp. 50–51.

In this respect, most drugs must have an affinity for water in order to be transported-by blood and other body fluids to their sites of action. One solution to the low water solubility of an active ingredient is to compound the active ingredient with emulsifiers or complexing agents to prevent the drug from precipitating at the site of administration. See *Human Pharmacology*, pp. 50–51. Any manipulation of the active ingredient, however, in an attempt to improve a physical property should not detrimentally affect its biological activity. The use of emulsifiers and complexing agents, while an acceptable approach, may limit the modes of administering the drug and/or render the drug more difficult to use and store.

There remains a need, therefore, for novel 5-aminoflavone compounds and compositions which exhibit potent antitumor properties. There also remains a need for 5-aminoflavone compounds which have improved solubility in water and organic solvents. The present invention provides such compounds, compositions, and methods. These and other advantages of the present invention, as well as additional inventive features, will be apparent from the description of the invention provided herein.

BRIEF SUMMARY OF THE INVENTION

The invention provides trifluoroaminoflavone compounds which are substituted with amine-containing groups at the 5- and/or 4'-position on the flavone ring, and optionally substituted with an alkyl, hydroxyalkyl, alkanoyloxyalkyl, alkanoyloxy, alkoxy, or alkoxyalkyl at the 7-position of the flavone ring, or pharmaceutically acceptable salts thereof. The compounds of the present invention demonstrate desirable physical characteristics, such as solubility in aqueous solvents.

In addition to their desirable physical properties, the aminoflavone compounds of the present invention also exhibit anti-tumor activity against a variety of cancer cells.

The present invention also provides a pharmaceutical composition comprising an aminoflavone compound as defined generally above, and a pharmaceutically acceptable carrier.

In another aspect, the present invention provides a method of inhibiting the growth of a tumor in a host by administering to the host a tumor growth-inhibiting amount of an aminoflavone compound as defined generally above. The host may be any mammal, including humans.

The invention may best be understood with reference to the accompanying drawings and in the following detailed description of the preferred embodiments.

DETAILED DESCRIPTION OF THE INVENTION

The present invention encompasses a novel class of aminoflavone compounds, compositions containing these compounds, and methods of using the compounds to inhibit the growth of tumors. Any suitable amine-containing moiety may be substituted at either or both of the $R^1$ and $R^2$ positions of Compound I, depicted below. Preferably, each of $R^1$ and $R^2$ is H, $COCH_2$—$R^7$, wherein $R^7$ is amino, branched or straight-chain alkylamino, dialkylamino, or alkyl- or dialkylaminoalkyl, or an α-amino acid residue, provided that at least one of $R^1$ or $R^2$ is other than H, and $R^3$ is H, branched or straight-chain alkyl, hydroxyalkyl, alkanoyloxyalkyl, alkanoyloxy, alkoxy, or alkoxyalkyl. Any suitable alkyl group may be substituted at $R^3$, including, for example, an alkyl group with from about 1 to about 20 carbon atoms, preferably from about 1 to about 15 carbon atoms, more preferably from about 1 to about 10 carbon atoms, and most preferably from about 1 to about 6 carbon atoms. As used herein, the term "alkyl" includes branched or straight-chain alkyl groups, such as methyl, ethyl, propyl, isopropyl, butyl, isobutyl, sec-butyl, tert-butyl, pentyl, isopentyl, neopentyl, hexyl, heptyl, and octyl.

Any suitable mono- or dialkylamino or mono- or dialkylaminoalkyl group may be substituted at $R^7$, including, for example, a group with an alkyl group with from about 1 to about 20 carbon atoms, preferably from about 1 to about 15 carbon atoms, more preferably from about 1 to about 10 carbon atoms, and most preferably from about 1 to about 6 carbon atoms. The term "alkyl" may include, for example, any of the groups listed previously.

Any suitable hydroxyalkyl group may be substituted at $R^3$, including, for example, a hydroxyalkyl group with from about 1 to about 20 carbon atoms, preferably with from about 1 to about 15 carbon atoms, more preferably from about 1 to about 10 carbon atoms, and most preferably from about 1 to about 6 carbon atoms. The term "alkyl" may include, for example, any of the groups listed previously.

Any suitable alkanoyloxy or alkanoyloxyalkyl may be substituted at $R^3$, including, for example, a group with from about 1 to about 20 carbon atoms, preferably from about 1 to about 15 carbon atoms, more preferably from about 1 to about 10 carbon atoms, and most preferably from about 1 to about 6 carbon atoms. The term "alkanoyloxy" may include branched or straight-chain groups, such as methanoyloxy, ethanoyloxy, propanoyloxy, butanoyloxy, pentanoyloxy, hexanoyloxy, heptanoyloxy, and octanoyloxy. The term "alkyl" may include, for example, any of the groups listed previously.

Any suitable alkoxy or alkoxyalkyl group may be substituted at $R^3$, including, for example, a group with from about 1 to about 20 carbon atoms, preferably from about 1 to about 15 carbon atoms, more preferably from about 1 to about 10 carbon atoms, and most preferably from about 1 to about 6 carbon atoms. The term "alkoxy" may include, for example, branched or straight-chain alkoxy groups, such as methoxy, ethoxy, propoxy, isopropoxy, butoxy, isobutoxy, sec-butoxy, tert-butoxy, pentoxy, hexoxy, heptoxy, and octoxy. The term "alkyl" may include, for example, any of the groups listed previously.

Any suitable α-amino acid residue, and derivatives thereof, may be substituted at $R^7$. Examples of such α-amino acid residues include naturally occurring amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. Suitable substituent groups and the compounds formed thereby include, for example, those outlined in Table 1 below.

TABLE 1

Representative Structures of Novel Aminoflavone Compounds (I)

| Cpd | $R^1$ | $R^2$ | $R^3$ |
|---|---|---|---|
| 1a | CO—CHNH$_2$—(CH$_2$)$_4$—NH$_2$ | H | CH$_3$ |
| 1b | CO—CHNH$_2$—(CH$_2$)$_3$—NH—C(NH)—NH$_2$ | H | CH$_3$ |
| 1c | CO—CH$_2$—N(CH$_3$)$_2$ | H | CH$_3$ |
| 1d | CO—CH$_2$—N(CH$_3$)$_2$ | CO—CH$_2$—N(CH$_3$)$_2$ | CH$_3$ |
| 1e | CO—CH$_2$—NH$_2$ | H | CH$_2$OH |
| 1f | CO—CH$_2$—N(CH$_3$)$_2$ | H | CH$_2$OAc |
| 1g | CO—CH$_2$—N(CH$_3$)$_2$ | H | CH$_2$OH |
| 1h | CO—(CH$_2$)$_2$—N(CH$_3$)$_2$ | H | CH$_2$OAc |
| 1i | CO—(CH$_2$)$_2$—N(CH$_3$)$_2$ | H | CH$_2$OH |
| 1j | CO—(CH$_2$)$_3$—N(CH$_3$)$_2$ | H | CH$_2$OAc |
| 1k | CO—(CH$_2$)$_3$—N(CH$_3$)$_2$ | H | CH$_2$OH |
| 1l | H | CO—CH$_2$—NH$_2$ | CH$_2$OH |
| 1m | H | CO—CH$_2$—N(CH$_3$)$_2$ | CH$_2$OH |
| 1n | H | CO—(CH$_2$)$_2$—N(CH$_3$)$_2$ | CH$_2$OH |

One of skill in the art will also appreciate that compounds of the present invention may be converted into pharmaceutically acceptable salts through the use of well-known and readily available reactions, reagents, and procedures.

In the aminoflavone compounds of the present invention, when each of $R^1$ or $R^2$ of structure I is an α-amino acid residue, the stereochemistry of $R^1$ and $R^2$ is preferably L. Examples of such compounds include 5-amino-6,8-difluoro-2-[3-fluoro-4-[(L-lysyl)amino]phenyl]-7-methyl-4H-1-benzopyran-4-one and 5-amino-2-[4-[[2-amino-5-guanidinopentanoyl]amino]-3-fluorophenyl]-6,8-difluoro-7-methyl-4H-1-benzopyran-4-one.

The substitution of an amine-containing moiety at $R^1$ and $R^2$ imparts a high solubility, in solvents such as water, to the compound. High water solubility is desirable and beneficial. In addition to the ease of administering water soluble compounds, high water solubility also increases absorption of the compounds after, for example, oral administration of the compounds to an individual or host. High water solubility is also beneficial when the compounds of the present invention are formulated into pharmaceutical products as an active ingredient in the composition.

Surprisingly, in addition to the solubility-enhancing properties, the amine-containing moieties at $R^1$ and $R^2$ on the compounds of the present invention also demonstrate some permanence and are not readily cleaved from the compound. The apparent persistence of these substituent groups may signify their contribution to the biological activity of the compounds, although the precise mechanism through which these groups influence biological activity is presently unknown.

The compounds of the present invention can be synthesized using well-known and readily available chemical reactions, reagents, and procedures. It will also be appreciated by one skilled in the art that compounds of the present invention, including antitumor derivatives and prodrugs thereof, may be obtained by chemical modification(s) of synthetic or naturally occurring compounds of the present invention, using well-known and readily available reactions, reagents, and procedures.

For example, Compound I can be prepared by, first, reacting a 7-substituted-5,4'-diamino-6,8,3'-trifluoroflavone with a suitably N-protected amino acid or its reactive derivative in the presence of a base and/or a condensing reagent, such as carbodiimide, carbonyldiimidazole, and the like, in an inert solvent. Examples of the reactive derivative of the suitably N-protected amino acid include an acid chloride, a N-hydroxysuccinimide ester and the like. As the base, tertiary amines such as triethylamine, diisopropylethylamine, pryidine, and 4-dimethylaminopyridine may be used. As the inert solvent, dimethylformamide, dichloromethane, chloroform, and the like may be used alone or in combination with each other. As the suitable N-protecting group of the amino acid, a butoxycarbonyl group, a benzyloxycarbonyl group, a 9-fluorenylmethoxycarbonyl group, and the like may be used. The reaction is carried out at a temperature between room temperature and the boiling point of the solvent. The resulting product, wherein $R^1$ and $R^2$ respectively are suitably protected, can then be transformed into Compound I by deprotection of the product by methods such as those described in *Protecting Groups in Organic Synthesis*, T. W. Green, ed., John Wiley & Sons, Inc. (1981).

Compound I can also be prepared by, first, reacting a 7-substituted-5,4'-diamino-6,8,3'-trifluoroflavone compound with an acid represented by the general formula HOOC—Y—X or its reactive derivative, wherein X represents chlorine, bromine, or iodine, and Y represents a $C_{1-20}$ branched or straight-chain alkyl, in a manner similar to that described above. The resulting product can then be reacted with sodium azide in an inert solvent. As the inert solvent, dimethylformamide, dimethylacetamide, dimethylsulfoxide, tetrahydrofuran, 1,2-dimethoxyethane, and the like may be used alone or in combination with each other. The reaction is carried out preferably at the temperature between 50–100° C. The final product may be obtained by reduction of the azido groups to amino groups by catalytic hydrogenation or by using triphenylphosphine and water in an inert solvent. As the catalyst, palladium on charcoal, palladium hydroxide, platinum oxide, and the like may be used. As the inert solvent, methanol, ethanol, propanol, ethyl acetate, tetrahydrofuran, 1,2-dimethoxyethane, toluene, dimethylformamide, dimethylacetamide, and the like may be used alone or in combination with each other. The reaction is preferably carried out at a temperature between 20–30° C.

Compound I, wherein $R_1$ is H, can also be prepared by, first, reacting a 7-substituted-5-amino-trifluoroflavone compound, wherein the 4'-amino is substituted with an allyloxycarbonyl group, with a suitably N-protected amino acid or its reactive derivative in a manner similar to that described previously. The final product can be obtained by, first, deprotecting the above compound, and then treating the resulting compound with tetrakis(triphenylphosphine)-palladium in the presence of a suitable reducing agent in an inert solvent. As the reducing agent, triethylammonium formate, pyrrolidine, and the like may be used. As the inert solvent, tetrahydrofuran, 1,2-dimethoxyethane, and the like may be used. The reaction is typically carried out at a temperature between 0° C. and room temperature. The order of the above procedures may be modified according to recognized principles and processes in the art.

The novel aminoflavone compounds of the present invention (and pharmaceutically acceptable salts thereof) can be included in a suitable composition, for example, a pharmaceutical composition. The composition can be produced by combining one or more compounds of the present invention with an appropriate pharmaceutically acceptable carreie, and can be formulate into a suitable preparation. Suitable preparations include, for example, preparations in solids, semi-solid, liquid, or gaseous forms such as tablets, capsules, powders, granules, ointments, solutions, suppositories, injections, inhalants, and aerosols, and other formulations known in the art for their respective routes of administration. In pharmaceutical dosage forms, a compound of the present invention can be used alone or in appropriate association as well as in combination, with other pharmaceutically active compounds, including other anti-tumor or anticancer agents.

Suitable anticancer agents include, for example, doxorubicin, bleomycin, vincristine, vinblastine, VP-16, VM-26, cisplatin, procarbazine, and taxol. Alkylating agents, such as BCNU, CCNU, methyl-CCNU, and DTIC, are also suitable. Antimetabolites, such as 5-FU and methotrexate, can also be used in the present inventive method. For further examples of suitable anticanver agents see Table 1 and 2 of Boyd In: *Current Therapy in Oncology*, J. E. Niederhuber, ed., Philadelphia: B. C. Decker, Inc., pp. 11–22 (1993).

Any suitable carrier can be utilized. Suitable carriers include pharmaceutically or physiologically acceptable carriers. The following methods and carriers are merely exemplary and are in no way limiting. In the case of oral preparations, a compound of the present invention can be administered alone or in combination with a therapeutically effective amount of at least one other compound. Compositions used in accordance with the present invention can further include at least one additional compound other than a compound of the present invention, for example, an additional anticancer agent. The active ingredient(s) can be combined, if desired, with appropriate additives to make tablets, powders, granules, capsules, or the like.

Suitable additives can include, for example, conventional additives such as lactose, mannitol, corn starch or potato starch. Suitable additives also can include binders, for example, crystalline cellulose, cellulose derivatives, acacia, corn starch, or gelatins. In addition, disintegrants, such as corn starch, potato starch or sodium carboxymethylcellulose, and lubricants, such as talc or magnesium stearate, can also be included. If desired, other additives such as, for example, diluents, buffering agents, moistening agents, preservatives, and/or flavoring agents, and the like, can be included in the composition.

The compounds of the present invention can be formulated into a preparation for injection by dissolution, suspension, or emulsification in an aqueous or nonaqueous solvent, such as vegetable oil, synthetic aliphatic acid glycerides, esters of higher aliphatic acids, or propylene glycol (if desired, with conventional additives such as solubilizers, isotonic agents, suspending agents, emulsifying agents, stabilizers, and preservatives). The compounds of the present invention also can be made into an aerosol formulation to be administered via inhalation. Such aerosol formulations can be placed into pressurized acceptable propellants such as dichlorodifluoromethane, propane, nitrogen, and the like.

Unit dosage forms for oral administration such as syrups, elixirs, and suspensions can be provided wherein each dosage unit, e.g., teaspoonful, tablespoonful, or tablet contains a predetermined amount of the composition containing the compound of the present invention. Similarly, unit dosage forms for injection or intravenous administration can comprise a composition as a solution in sterile water, normal saline, or other pharmaceutically acceptable carrier.

The term "unit dosage form" as used herein refers to physically discrete units suitable as unitary dosages for human and animal subjects, each unit containing a predetermined quantity of at least one compound or compounds of the present invention (alone or, if desired, in combination with another therapeutic agent). The unit dosage can be determined by methods known to those of skill in the art, for example, by calculating the amount of active ingredient sufficient to produce the desired effect in association with a pharmaceutically acceptable carrier. The specifications for the unit dosage forms that can be used in accordance with the present invention depend on the particular effect to be achieved and the particular pharmacodynamics associated with the compound(s) in the individual host.

Pharmaceutically acceptable carriers, for example, vehicles, adjuvants, excipients, or diluents, are accessible to those of skill in the art and are typically available commercially. One skilled in the art can easily determine the appropriate method of administration for the exact formulation of the composition being used. Any necessary adjustments in dose can be readily made by a skilled practitioner to address the nature or severity of the condition being treated. Adjustments in dose also can be made on the basis of other factors such as, for example, the individual patient's overall physical health, sex, age, prior medical history, and the like.

The present invention also provides a method of inhibiting the growth of a tumor in a host, including a human, comprising administering to the host a tumor growth-inhibiting amount of an aminoflavone compound of the present invention. The present inventive method also includes the administration of aminoflavone compounds of the present invention (and pharmaceutically acceptable salts thereof) together with a pharmaceutically acceptable carrier. Further, the method of the present invention includes administering an aminoflavone compound of the present invention with a pharmaceutically acceptable carrier and/or at least one other anticancer agent. Any suitable anticancer agent can be used in conjunction with the compounds of the present invention, as described previously.

Aminoflavone compounds of the present invention can be administered to the host. Desirably, the aminoflavone compounds administered to a host include, for example, those listed in Table 1. The preferred aminoflavone compounds for administering to a host are 5-amino-6,8-difluoro-2-[3-fluoro-4-[(L-lysyl)amino)]phenyl]-7-methyl-4H-1-benzopyran-4-one, 5-amino-2-[4-[[2-amino-5-guanidinopentanoyl]amino]-3-fluorophenyl]-6,8-difluoro-7-methyl-4H-1-benzopyran-4-one, 6,8-difluoro-7-methyl-5-(dimethylamino)acetamido-2-[4-(dimethylamino)acetamido-3-fluorophenyl]-4H-1-benzopyran-4-one, and 5-amino-6,8-difluoro-7-methyl-2-[4-(dimethylamino)acetamido-3-fluorophenyl]-4H-1-benzopyran-4-one. Particularly preferred is 5-amino-6,8-difluoro-2-[3-fluoro-4-[(L-lysyl)amino)]phenyl]-7-methyl-4H-1-benzopyran-4-one, dimethanesulfonate.

The compounds of the present invention can be administered by any suitable route including, for example, oral administration, intramuscular administration, subcutaneous administration, intravenous administration, or the like. For example, one or more aminoflavone compounds of the present invention (or a composition thereof) can be administered as a solution that is suitable for intravenous injection or infusion, a tablet, a capsule, or the like, or in any other suitable composition or formulation as described herein.

The "tumor growth-inhibiting amount" is the dose necessary to achieve a tumor growth "inhibiting level" of the active compound in an individual patient. The tumor growth-inhibiting amount can be defined, for example, as that amount required to be administered to an individual patient to achieve a tumor growth-inhibiting blood level, tissue level, and/or intracellular level of a compound of the present invention to effect the desired medical treatment.

When the effective level is used as the preferred endpoint for dosing, the actual dose and schedule can vary depending, for example, upon interindividual differences in pharmacokinetics, drug distribution, metabolism, and the like. The effective level also can vary when one or more compounds of the present invention are used in combination with other anticancer agents. Moreover, the effective level can vary depending upon the disease for which treatment is desired.

In this respect, the compounds and compositions of the present invention may also be used as antibacterial agents and/or as anti-estrogen agents. One of ordinary skill in the art may use any suitable means known in the art to determine the appropriate dosage and effective level of the compound or composition of the present invention based upon the disease for which treatment is desired.

To the extent that the compounds are used in accordance with the present invention as anticancer agents, the effective blood level can be determined by analogy based on the effective blood level corresponding to anticancer activity. The effective level can be chosen, for example, as that level effective to inhibit the proliferation of tumor cells in a screening assay. Similarly, the effective level can be determined, for example, on the basis of the blood or tissue level in a patient that corresponds to a concentration of a therapeutic agent that effectively inhibits the growth of human cancers in an assay that is clinically predictive of anticancer activity. Further, the effective level can be determined, for example, based on a concentration at which certain markers of cancer in a patient's blood are inhibited by a particular compound. Alternatively, the effective level can be determined, for example, based on a concentration effective to slow or stop the growth of a patient's cancer, cause a patient's cancer to regress or disappear, render a patient asymptomatic to a particular cancer, or improve a cancer patient's subjective sense of condition.

The anticancer effective level can then be used to approximate (e.g., by extrapolation), or even to determine, the level which is required clinically to achieve a tumor growth-inhibiting blood, tissue, and/or intracellular level to effect the desired medical treatment. It will be appreciated that the determination of the therapeutically effective amount clinically required to effectively inhibit tumor growth requires consideration of other variables that can influence the effective level. When a fixed effective amount is used as a preferred endpoint for dosing, the actual dose and dosing schedule for drug administration can vary for each patient depending upon factors that include, for example, interindividual differences in pharmacokinetics, drug disposition, metabolism, or other factors described herein that effect the effective level.

One skilled in the art can readily determine the appropriate dose, schedule, or method of administering a particular formulation, in order to achieve the desired effective level in an individual patient. One skilled in the art also can readily determine and use an appropriate indicator of the effective level of the compounds of the present invention. For example, the effective level can be determined by direct analysis (e.g., analytical chemistry) or by indirect analysis (e.g., with clinical chemistry indicators) of appropriate patient samples (e.g., blood or tissue). The effective level also can be determined, for example, by direct or indirect observations such as urine acidity, change in bone density, decrease in ocular pressure, or by the shrinkage of a tumor in a cancer patient. There are many references in the art that describe protocols used in administering active compounds to a patient in need thereof. For example, the protocols used in the administration of anticancer agents to patients are described, e.g., in Cancer Chemotherapy: Principles and Practice, Chabner and Collins, eds., J. B. Lippincott, (1990) (particularly chapter 2).

The unique tumor growth-inhibiting activity of the compounds of the present invention has been demonstrated using the U.S. National Cancer Institute's (NCI's) 60 cell-line human tumor disease-oriented screen, which can accurately predict the anticancer activity of chemical compounds.

The NCI 60 cell-line human tumor screen measures the ability of a compound to selectively kill or inhibit the growth of diverse human cancers. Generally, in the NCI screen, the compounds of the present invention display potent activity against certain types of human solid tumors (e.g., non-small cell lung cancer, renal cancer, and melanoma), and resistant strains thereof. By these observations, and with other detailed analyses of the characteristic tumor cellular response profiles, it can be shown that the compounds of the present invention have a uniquely characteristic bioactivity profile.

The novel aminoflavone compounds of the present invention, in addition to their desirable solubility characteristics, also demonstrate potent tumor growth-inhibiting activities for a variety of human cancers, such as those tested in the NCI 60 cell-line screen. For example, compounds 1a–d from Table 1, or pharmaceutically acceptable salts thereof, all exhibited tumor growth inhibition in vitro, especially against human breast, ovarian, colon, and renal cancer cell lines. They also demonstrated tumor growth-inhibiting activity against certain human leukemia, non-small-lung cancer, and melanoma cell lines. See FIGS. 1a–e. For further illustration of the tumor growth-inhibition activity of the compounds of the present invention, see Example 16.

The following examples further illustrate the present invention but, of course, should not be construed as in any way limiting its scope. The mass spectral data for the compounds described in the following examples were determined either by Electrospray Ionization Mass-Spectrometry ("ESI-MS")(Examples 1–5) or by Fast Atom Bombardment Mass Spectrometry ("FABMS") (Examples 6–15 and 18–20).

EXAMPLE 1

This Example demonstrates the preparation of 5-amino-6,8-difluoro-2-[3-fluoro-4-[(L-lysyl)amino]phenyl]-7-methyl-4H-1-benzopyran-4-one, trihydrobromide (1a).

To a stirring solution of $N^2,N^6$-(dicarbobenzyloxy)-L-lysine (187 mg, 0.45 mmol) in tetrahydrofuran (6.0 mL) at 3° C. under argon was added oxalyl chloride (41 μL, 0.47 mol) and N,N-dimethylformamide (10 μL). After 15 minutes at 3° C., a cold solution of 5,4'-diamino-7-methyl-6,8,3'-trifluoro-4H-1-benzopyran-4-one (100 mg, 0.31 mmol) in N,N-dimethylformamide (2.4 mL) was added thereto. The mixture was stirred at 3° C. for 15 minutes and then at ambient temperature for 1.5 hours. The reaction mixture was partitioned between EtOAc (75 mL) and water (10 mL). The layers were separated and the water layer was extracted with $CH_2Cl_2$ (3×100 mL). The combined organic layer was dried ($MgSO_4$), filtered, then concentrated to give the crude product. A duplicate reaction was run and the crude material combined and purified by column chromatography on silica gel (step gradient elution from 1:1 to 3:2 EtOAc:hexane) to give 91 mg (20%) of purified product (i.e., 5-amino-4'-[$N^2$, $N^6$-(dicarbobenzyloxy)-L-lysinamido]-7-methyl-6,8,3'-trifluoro-4H-1-benzopyran-4-one, hereinafter "product 1"). Additional reactions were performed to give a total of 236 mg of similar material.

A solution of product 1 (90 mg, 0.13 mmol) in hydrogen bromide, 30% w/w solution in acetic acid (5 mL) was stirred at ambient temperature for 2 hours under argon. The reaction mixture was diluted with $Et_2O$ (40 mL) to give a suspension, and the solid was isolated by centrifugation. The solid was washed with $Et_2O$ (5×15 mL) via centrifugation then dried over argon, then in vacuo at ambient temperature for 5 hours, to give 80 mg (92%) of 5-amino-6,8-difluoro-2-[3-fluoro-4-[(L-lysyl)amino]phenyl]-7-methyl-4H-1-benzopyran-4-one, trihydrobromide. Additional reactions were performed to give a total of 113 mg of similar product.

Calculated for $C_{22}H_{26}F_3N_4O_3Br_3 \cdot 1.3H_2O$, C, 36.98; H, 4.03; N, 7.84; Br, 33.54. Found: C, 37.06/36.97,; H, 4.08/4.13; N, 7.66/7.59; Br, 32.59.

EXAMPLE 2

This Example illustrates the preparation of 5-amino-6,8-difluoro-2-[3-fluoro-4-[(L-lysyl)amino]phenyl]-7-methyl-4H-1-benzopyran-4-one, dimethanesulfonate (1a).

To a stirring solution of $N^2,N^6$-(dicarbobenzyloxy)-L-lysine (1.94 g, 4.68 mmol) in tetrahydrofuran (40 mL) at 0° C. under argon was added oxalyl chloride (412 µL, 4.72 mmol) and N,N-dimethylformamide (76 µL). After 15 minutes at 0° C., a cold solution of 5-amino-2-(4-amino-3-fluorophenyl)-6,8-difluoro-7-methyl-4H-1-benzopyran-4-one (1.0 g, 3.12 mmol) in N,N-dimethylformamide (20 mL) was added thereto. The mixture was stirred at 0° C. for 15 minutes and then at ambient temperature for 30 minutes. The reaction mixture was partitioned between EtOAc (1.0 L) and water (1.0 L). The layers were separated and the organic layer was dried, filtered, then concentrated to give the crude product (4.8 g). A total of 10×1 g runs of the aminoflavone were carried out to give a total of 49.4 g of material containing the intermediate 5-amino-4'-[$N^2,N^6$-(dicarbobenzyloxy)-L-lysinamido]-7-methyl-6,8,3'-trifluoro-4H-1-benzopyran-4-one. This material was chromatographed on a silica gel column (3 kg) packed in EtOAc/hexane (3:2) then eluted with EtOAc/hexane/DMF (60:40:1). Fractions containing pure product were combined, then concentrated in vacuo to a residue. This material was triturated with Et$_2$O (approx. 20 mL) to give 2.8 g (13%) of purified intermediate suitable for transformation.

The intermediate (1.50 g, 2.09 mmol) was dissolved in methanesulfonic acid (100 mL). The reaction mixture was stirred at room temperature for 24 hours. During this time color changes occurred, and finally a finely divided solid was formed. The reaction mixture was blended into EtOAc (500 mL). The resulting solution was clarified through fiber glass paper then concentrated in vacuo to a residue. This material was stirred with Et$_2$O (700 mL). After −10° C. cold storage, the Et$_2$O was decanted from a gummy solid and discarded. The solid material was dissolved in methanol (300 mL), clarified, concentrated in vacuo to the cloud point, then blended into Et$_2$O (600 mL). The precipitated product was collected by centrifugation. The process of methanol dissolution, ether precipitation, and centrifugal collection was repeated. A total of 3.25 g of intermediate was processed in a similar way to give 2.6 g (90%) of 5-amino-6,8-difluoro-2-[3-fluoro-4-[(L-lysyl)amino]phenyl]-7-methyl-4H-1-benzopyran-4-one, dimethanesulfonate.

Calculated for $C_{22}H_{23}F_3N_4O_3 \cdot 2CH_3SO_3H \cdot H_2O$, C, 43.76; H, 5.05; N, 8.51; S, 9.74. Found: C, 43.45; H, 4.89; N, 8.24; S, 9.90.

EXAMPLE 3

This Example illustrates the preparation of 5-amino-2-[4-[[2-amino-5-guanidinopentanoyl]amino]-3-fluorophenyl]-6,8-difluoro-7-methyl-4H-1-benzopyran-4-one, trihydrobromide (1b).

To a stirring solution of Nα,$N^G$,$N^{G'}$-(tricarbobenzyloxy)-L-arginine (5.4 g, 9.4 mmol) in tetrahydrofuran (60 mL) at 0° C. under argon was added oxalyl chloride (875 µL, 10.0 mmol) and N,N-dimethylformamide (50 µL). After 15 minutes at 0° C., a cold solution of 5,4'-diamino-7-methyl-6,8,3'-trifluoro-4H-1-benzopyran-4-one (1.0 g, 3.12 mmol) in N,N-dimethylformamide (30 mL) was added thereto. The mixture was stirred at 0° C. for 15 minutes and then at ambient temperature for 1 hour. The reaction mixture was partitioned between EtOAc (200 mL) and water (200 mL). The layers were separated, and the water layer was extracted with CH$_2$Cl$_2$ (5×100 mL). The combined organic layer was dried (MgSO$_4$), filtered, then concentrated to give the crude product. The crude product was purified by column chromatography on silica gel (step gradient elution from 1:2 to 1:1 EtOAc:hexane) to give 93 mg (3%) of purified product (i.e., 5-amino-4'-[Nα,$N^G$,$N^{G'}$-(tricarbobenzyloxy)-L-argininamido]-7-methyl-6,8,3'-trifluoro-4H-1-benzopyran-4-one, hereinafter "product 2").

A solution of product 2 (90 mg, 0.10 mmol) in hydrogen bromide, 30% w/w solution in acetic acid (5 mL) was stirred at ambient temperature for 24 hours under argon. The reaction mixture was diluted with Et$_2$O (40 mL) to give a suspension, and the solid was isolated by centrifugation. The solid was washed with Et$_2$O (5×20 mL) via centrifugation then dried over argon, then in vacuo at ambient temperature for 8 hours, to give 36 mg of the final product.

$C_{22}H_{23}F_3N_6O_3$=476 (free base). Found: 477.2 (M+H)$^+$.

EXAMPLE 4

This Example illustrates the preparation of 6,8-difluoro-7-methyl-5-(dimethylamino)acetamido-2-[4-(dimethylamino)acetamido-3-fluorophenyl]-4H-1-benzopyran-4-one (1d).

To a stirring solution of 5,4'-diamino-7-methyl-6,8,3'-trifluoro-4H-1-benzopyran-4-one (500 mg, 1.56 mmol) and 1,8-diazabicyclo[5.4.0]undec-7-ene (DBU) (254 µL, 1.70 mmol) in tetrahydrofuran (25 mL) under argon was added a 2.51 mol/L solution of chloroacetyl chloride in tetrahydrofuran (640 µL, 1.61 mmol). After 1 hour at room temperature, additional DBU (64 µL) and 2.51 mol/L chloroacetyl chloride (160 µL) were added. After an additional 30 minutes at room temperature, more DBU (64 µL) and 2.51 mol/L chloroacetyl chloride (160 µL) were added. After 40 minutes at room temperature, a final aliquot of DBU and choroacetyl chloride were added. After 15 minutes, the TLC showed the reaction to be completed. The reaction mixture was filtered and the gummy residue was washed with tetrahydrofuran (2×20 mL). The combined filtrate and washings contained the crude product 5,4'-bis(chloroacetamido)-7-methyl-6,8,3'-trifluoro-4H-1-benzopyran-4-one (hereinafter "product 3").

To a stirring solution of product 3 in tetrahydrofuran (65 mL) was added dimethylamine gas for five minutes to give a saturated solution. The mixture was stirred at room temperature for 1 hour, then concentrated to give a yellow solid (0.7 g). The solid was dissolved in hot EtOAc (300 mL) and purified on a pad of silica gel. Product fractions yielded a yellow solid which was triturated with a mixture of EtOAc (25 mL) and hexane (100 mL), then suction filtered. The solid was washed with hexane (2×25 mL) then dried in vacuo at 40° C. for six hours to give 330 mg (52%) of the final product.

$C_{24}H_{25}F_3N_4O_4$=490.2. Found: 491.2 (M+H)$^+$.

EXAMPLE 5

This Example illustrates the preparation of 5-amino-6,8-difluoro-7-methyl-2-[4-(dimethylamino)acetamido-3-fluorophenyl]-4H-1-benzopyran-4-one (1c).

To a stirring solution of 5,4'-diamino-7-methyl-6,8,3'-trifluoro-4H-1-benzopyran-4-one (1.5 g, 4.68 mmol) and 1,8-diazabicyclo[5.4.0]undec-7-ene. (DBU) (2961 µL 19.8 mmol) in tetrahydrofuran (150 ml) under argon was added a 2.51 mol/L solution of chloroacetyl chloride in tetrahydrofuran (7.5 mL, 18.8 mmol). After 3 hours at room temperature, additional DBU (1.7 mL) and 2.51 mol/L chloroacetyl chloride (4.5 mL) were added and the mixture was stirred at room temperature for 20 hours. The reaction mixture was filtered and the gummy residue was washed with tetrahydrofuran (2×50 mL). The combined filtrate and washings contained the crude product 5-amino-4'-chloroacetamido-7-methyl-6,8,3'-trifluoro-4H-1-benzopyran-4-one (hereinafter "product 4").

To a stirring solution of product 4 (approx. 2.2 g, 4.68 mmol) in tetrahydrofuran (250 mL) was added dimethylamine gas for 10 minutes to give a saturated solution. The mixture was stirred at room temperature for 4.5 hours, then concentrated to dryness. The residue was purified on a column of silica gel (180 g, 3×25 cm) eluted with 15:1 EtOAc:MeOH, to give a solid. The solid was triturated with hexane (100 mL), suction filtered and dried in vacuo at 40° C. for six hours to give 1.09 g (47%) of the final product.

$C_{20}H_{18}F_3N_3O_3$=405.1. Found: 406.0 (M+H)$^+$.

EXAMPLE 6

This Example illustrates the preparation of 5-amino-2-[4-(aminoacetamido)-3-fluorophenyl]-6,8-difluoro-7-(hydroxymethyl)-4H-1-benzopyran-4-one (1e).

To a solution of 7-(acetoxymethyl)-5-amino-2-[4-(chloroacetamido)-3-fluorophenyl]-6,8-difluoro-4H-1-benzopyran-4-one (1.00 g, 2.20 mmol) in dimethylformamide (50 mL) was added sodium azide (715 mg, 11 mmol), and the mixture was stirred at room temperature for 1 hour. Water was added thereto, and the crystals precipitated were collected by filtration to afford 7-(acetoxymethyl)-5-amino-2-[4-(azidoacetamido)-3-fluorophenyl]-6,8-difluoro-4H-1-benzopyran-4-one (1.01 g, 100%).

To a suspension of the above compound (1.00 g, 2.17 mmol) in methanol (100 mL) was added 1 mol/L potassium carbonate (10 mL), and the mixture was stirred at room temperature for 25 minutes. The pH was adjusted to 7 with 1 mol/L HCl. Water was added, and the crystals precipitated were collected by filtration to afford 5-amino-2-[4-(azidoacetamido)-3-fluorophenyl]-6,8-difluoro-7-(hydroxymethyl)-4H-1-benzopyran-4-one (764 mg, 84%).

To a solution of the above compound (750 mg, 1.79 mmol) in ethyl acetate (300 mL) and methanol (150 mL) was added palladium on charcoal (10%, 350 ml), and the mixture was stirred under hydrogen flow at room temperature for 1.5 hours. After the hydrogen was replaced with nitrogen, the mixture was filtered through a Celite pad. The solvent was evaporated under reduced pressure and the residue was purified by silica gel column chromatography to afford a free base of 1e (460 mg, 65%), which was converted into a hydrochloride.

$C_{18}H_{14}F_3N_3O_4$=393. Found: 394 (M+H)$^+$.

EXAMPLE 7

This Example illustrates the preparation of 7-(acetoxymethyl)-5-amino-6,8-difluoro-2-[4-(dimethylamino) acetamido-3-fluorophenyl]-4H-1-benzopyran-4-one (1f).

To a solution of 7-(acetoxymethyl)-5-amino-2-[4-(chloroacetamido)-3-fluorophenyl]-6,8-difluoro-4H-1-benzopyran-4-one (2.02 g, 4.44 mmol) in dimethylformamide (50 mL) were added dimethylamine hydrochloride (1.81 g, 22.2 mmol) and diisopropylethylamine (3.90 mL, 22.4 mmol), and the mixture was stirred at room temperature for 2 hours. Water was added thereto, and the crystals precipitated were collected by filtration to afford compound 1f (1.97 g, 96%).

$C_{22}H_{20}F_3N_3O_5$=463. Found: 464 (M+H)$^+$.

EXAMPLE 8

This Example illustrates the preparation of 5-amino-6,8-difluoro-2-[4-(dimethylamino)acetamido-3-fluorophenyl]-7-(hydroxymethyl)-4H-1-benzopyran-4-one (1 g).

To a suspension of compound 1f (1.97 g, 4.25 mmol) in methanol (135 mL) was added 1 mol/L sodium hydroxide (15 ml), and the mixture was stirred at room temperature. Water was added thereto, and the crystals precipitated were collected by filtration. Purification by silica gel column chromatography (9:1 chloroform/methanol) gave a free base of 1g (834 mg, 47%), which was converted into a hydrochloride.

$C_{20}H_{18}F_3N_3O_4$=421. Found: 422 (M+H)$^+$.

EXAMPLE 9

This Example illustrates the preparation of 7-(acetoxymethyl)-5-amino-2-[4-[[3-(dimethylamino)propionyl]amino]-3-fluorophenyl]-6,8-difluoro-4H-1-benzopyran-4-one (1 h).

To a solution of 7-(acetoxymethyl)-5-amino-2-[4-amino-3-fluorophenyl]-6,8-difluoro-4H-1-benzopyran-4-one (1.51 g, 4.00 mmol) in dimethylformamide (40 mL) were added 3-bromopropionic acid (3.06 g, 20.0 mmol) and 1-[3-(dimethylamino)propyl]-3-ethylcarbodiimide hydrochloride (3.83 g, 20.0 mmol), and the mixture was stirred at room temperature for 45 minutes. Water was added thereto and the mixture was extracted with ethyl acetate. Purification by silica gel column chromatography (6:1 chloroform/acetate) gave 7-(acetoxymethyl)-5-amino-2-[4-[(3-bromopropionyl)amino]-3-fluorophenyl]-6,8-difluoro-4H-1-benzopyran-4-one (554 mg, 27%).

To a solution of the above compound (500 mg, 0.975 mmol) in dimethylformamide (15 mL) were added dimethylamine hydrochloride (397 mg, 4.87 mmol) and diisopropylethylamine (0.85 mL, 4.88 mL), and the mixture was stirred at 50° C. for 1 hour. Water was added thereto, and the mixture was extracted with ethyl acetate. Purification by silica gel column chromatography (20:1 chloroform/methanol) gave 1 h (442 g, 95%).

$C_{23}H_{22}F_3N_3O_5$=477. Found: 478 (M+H)$^+$.

EXAMPLE 10

This Example illustrates the preparation of 5-amino-6,8-difluoro-2-[4-[[3-(dimethylamino)propionyl]amino]-3-fluorophenyl]-7-(hydroxymethyl)-4H-1-benzopyran-4-one (1i).

To a suspension of 1 h (400 mg, 0.839 mmol) in methanol (36 mL) was added 1 mol/L sodium hydroxide (4 mL), and the mixture was stirred at room temperature for 20 minutes. Water was added thereto, and the crystals precipitated were collected by filtration. Purification by silica gel column chromatography (9:1 chloroform/methanol) gave a free base of 1i (365 mg, 100%), which was converted into a hydrochloride.

$C_{21}H_{20}F_3N_3O_4$=435. Found: 436 (M+H)$^+$.

EXAMPLE 11

This Example illustrates the preparation of 7-(acetoxymethyl)-5-amino-6,8-difluoro-2-[4-[[4-(dimethylamino)butyryl]amino]-3-fluorophenyl]-4H-1-benzopyran-4-one (1j).

To a solution of 7-(acetoxymethyl)-5-amino-2-[4-amino-3-fluorophenyl]-6,8-difluoro-4H-1-benzopyran-4-one (500 mg, 1.32 mmol) in dimethylformamide (15 mL) were added 4-dimethylaminobutyric acid hydrochloride (3.06 g, 16.9 mmol) and 1-[3-(dimethylamino)propyl]-3-ethylcarbodiimide hydrochloride (3.23 g, 16.9 mmol), and the mixture was stirred at room temperature for 2.5 hours. Water was added thereto, and the mixture was extracted with ethyl acetate. Purification by silica gel column chromatography (9:1 chloroform/methanol) gave 1j (386 mg, 60%).

$C_{24}H_{24}F_3N_3O_5$=491. Found: 492 (M+H)$^+$.

EXAMPLE 12

This Example illustrates the preparation of 5-amino-6,8-difluoro-2-[4-[[4-(dimethylamino)butyryl]amino]-3-fluorophenyl]-7-(hydroxymethyl)-4H-1-benzopyran-4-one (1k).

To a suspension of 1j (363 mg, 0.739 mmol) in methanol (36 mL) was added 1 mol/L sodium hydroxide (4 mL), and the mixture was stirred at room temperature for 20 minutes. Water was added thereto and the crystals precipitated were collected by filtration. Purification by silica gel column chromatography gave a free base of 1k (299 mg, 69%), which was converted into a hydrochloride.

$C_{22}H_{22}F_3N_3O_4$=449. Found: 450 (M+H)$^+$.

EXAMPLE 13

This Example illustrates the preparation of 5-(aminoacetamido)-2-(4-amino-3-fluorophenyl)-6,8-difluoro-7-(hydroxymethyl)-4H-1-benzopyran-4-one (1l).

To a solution of 2-[4-(allyloxycarbonyl)amino-3-fluorophenyl]-7-[((allyloxycarbonyl)oxy]methyl-5-(chloroacetamido)-6,8-difluoro-4H-1-benzopyran-4-one (1.16 g, 2.00 mmol) in dimethylformamide (20 mL) was added sodium azide (650 mg, 10.0 mmol), and the mixture was stirred at room temperature for 1 hour. Water was added thereto, and the crystals precipitated were collected by filtration to afford 7-[(allyloxycarbonyl)oxy]methyl-5-(azidoacetamido)-2-[4-(allyloxycarbonyl)amino-3-fluorophenyl]-6,8-difluoro-4H-1-benzopyran-4-one (1.01 g, 100%).

To a solution of the above compound (877 mg, 1.49 mmol) in tetrahydrofuran (30 mL) were added triethylammonium formate (1.2 mL, 9.1 mmol) and tetrakis(triphenylphosphine)palladium(0) (172 mg, 0.15 mmol) under argon atmosphere, and the mixture was stirred at room temperature for 50 minutes. Water was added thereto, and the mixture was extracted with ethyl acetate. Purification by silica gel column chromatography (20:1 chloroform/methanol) gave 5-(azidoacetamido)-2-(4-amino-3-fluorophenyl)-6,8-difluoro-7-(hydroxymethyl)-4H-1-benzopyran-4-one (560 mg, 90%).

To a solution of the above compound (540 mg, 1.30 mmol) in ethyl acetate (150 mL) and methanol (50 ml) was added palladium on charcoal (10%, 250 ml), and the mixture was stirred under hydrogen flow at room temperature for 2 hours. After the hydrogen was replaced with nitrogen, the mixture was filtered through a Celite pad. The solvent was evaporated under reduced pressure and the residue was purified by silica gel column chromatography (9:1:1 chloroform/methanol/ammonia) to afford a free base of 1l (330 mg, 65%), which was converted into a hydrochloride.

$C_{18}H_{14}F_3N_3O_4$=393. Found: 394 (M+H)$^+$.

EXAMPLE 14

This Example illustrates the preparation of 2-(4-amino-3-fluorophenyl)-5-(dimethylamino)acetamido-6,8-difluoro-7-(hydroxymethyl)-4H-1-benzopyran-4-one (1m).

To a solution of 2-[4-(allyloxycarbonyl)amino-3-fluorophenyl]-7-[((allyloxycarbonyl)oxy]methyl-5-(chloroacetamido)-6,8-difluoro-4H-1-benzopyran-4-one (2.12 g, 3.65 mmol) in dimethylformamide (40 mL) were added dimethylamine hydrochloride (1.49 g, 18.3 mmol) and diisopropylethylamine (3.2 mL, 18 mmol), and the mixture was stirred at 50° C. for 2 hours. Water was added thereto, and the mixture was extracted with ethyl acetate to afford 2-[4-(allyloxycarbonyl)amino-3-fluorophenyl]-7-[(allyloxycarbonyl)oxy]methyl-5-(dimethylamino)acetamido-6,8-difluoro-4H-1-benzopyran-4-one (2.12 g, 99%)

To a solution of the above compound (2.12 mg, 3.60 mmol) in tetrahydrofuran (50 mL) were added triethylammonium formate (2.4 mL, 18 mmol) and tetrakis(triphenylphosphine)palladium(0) (419 mg., 0.36 mmol) under argon atmosphere, and the mixture was stirred at room temperature for 1.5 hours. Water was added thereto, and the mixture was extracted with ethyl acetate. Purification by silica gel column chromatography (20:1 chloroform/methanol) gave a free base of 1m (1.05 g, 69%), which was converted into a hydrochloride.

$C_{20}H_{18}F_3N_3O_4$=421. Found: 422 (M+H)$^+$.

EXAMPLE 15

This Example illustrates the preparation of 2-[4-amino-3-fluorophenyl]-6,8-difluoro-5-[3-(dimethylamino)propionyl]amino-7-(hydroxymethyl)-4H-1-benzopyran-4-one (1n).

To a solution of 2-[4-(allyloxycarbonyl)amino-3-fluorophenyl]-7-[(allyloxycarbonyl)oxy]methyl-5-amino-6,8-difluoro-4H-1-benzopyran-4-one (1.00 g, 1.90 mmol) in dimethylformamide (30 mL) were added 3-bromopropionic acid (3.04 g, 19.9 mmol) and 1-[3-(dimethylamino)propyl]-3-ethylcarbodiimide hydrochloride (3.80 g, 19.8 mmol), and the mixture was stirred at room temperature for 8 hours. Water was added thereto, and the mixture was extracted with ethyl acetate to afford a crude 0.2-[4-allyloxycarbonyl)amino-3-fluorophenyl]-7-[(allyloxycarbonyl)oxy]methyl-5-[(3-bromopropionyl)amino]-6,8-difluoro-4H-1-benzopyran-4-one (1.98 g).

To a solution of the above compound (1.98 mg) in dimethylformamide (20 mL) were added dimethylamine hydrochloride (807 mg, 9.90 mmol) and diisopropylethylamine (1.7 mL, 9.93 mmol), and the mixture was stirred at 50° C. for 7 hours. Water was added thereto, and the mixture was extracted with ethyl acetate. Purification by silica gel column chromatography (20:1 chloroform/methanol) gave 2-[4-(allyloxycarbonyl)amino-3-fluorophenyl]-7-[(allyloxycarbonyl)oxy]methyl-5-[[3-(dimethylamino)propionyl]amino]-6,8-difluoro-4H-1-benzopyran-4-one.

To a solution of the above compound (688 mg, 1.14 mmol) in tetrahydrofuran (20 mL) were added triethylammonium formate (0.75 mL, 5.7 mmol) and tetrakis(triphenylphosphine)palladium (0) (132 mg, 0.11 mmol) under argon atmosphere, and the mixture was stirred at room temperature for 1.5 hours. Water was added thereto and the mixture was extracted with ethyl acetate. Purification by silica gel column chromatography gave a free base of In (74 mg, 15%), which was converted into a hydrochloride.

$C_{21}H_{20}F_3N_3O_4$=435. Found: 436 (M+H)$^+$.

EXAMPLE 16

This Example illustrates the tumor growth-inhibiting activity of the novel aminoflavone compounds of the present invention, specifically the activity demonstrated by 5-amino-6,8-difluoro-2-(3-fluoro-4-[(L-lysyl)amino]phenyl]-7-methyl-4H-1-benzopyran-4-one (compound 1a in Table 1).

As noted previously, the compounds of the present invention were tested in the NCI 60 cell-line screen. The NCI 60 cell-line human tumor primary screen provides a means by which to identify natural sources of compounds. The NCI screen was designed and implemented during 1985–1990 under the direction, close scrutiny, and supervision of several internationally comprised and renowned extramural (non-NCI) advisory and review groups, including the NCI Division of Cancer Treatment's Board of Scientific Counselors, an Ad Hoc Expert Review Committee thereof, the National Cancer Advisory Board, and the President's Cancer Panel. See Boyd, In: *Anticancer Drug Development Guide: Preclinical Screening, Clinical Trials*, and Approval, Teicher, B. A., ed., Totowa, N.J.: Humana Press, Inc., pp. 23–42 (1997). Although the NCI screen has been operational only since 1990, it has already led to the discovery, development, and clinical use of significant new anticancer drugs in human cancer patients. See, e.g., Weinstein et al., *Science*, 275, 343–349 (1997); Grever and Chabner, In: *Cancer: Principles and Practice of Oncology*, 5$^{th}$ Ed., DeVita et al., eds., Philadelphia: Lippincott-Raven, pp. 385–394 (1997).

The NCI screen consists of a panel of 60 different human tumor cell lines against which compounds are tested over a defined range of concentrations to determine the relative degree of growth inhibition or cytotoxicity against each cell line. The design and operation of the screen is such that for each compound tested, both the absolute and relative sensitivities of individual cell lines comprising the screen are sufficiently reproducible that a characteristic profile or "fingerprint" of cellular response is generated. Compounds that are active in the NCI screen show pronounced differential tumor growth-inhibitory and/or cytotoxic effects to the diverse cell lines comprising the 60 cell-line panel. The degree of differential response between the most and least sensitive lines typically may be relatively small (e.g., 2–10 fold), or occasionally as great as 3–4 orders of magnitude. Furthermore, the cell lines may be widely heterogeneous in response to a given compound, or they may be comparatively homogeneous, with only a relatively few lines showing much greater or lesser sensitivity than average. Regardless of the magnitude of the differential or the degree of heterogeneity of response of the cell line panel, it is the reproducibility of the response "fingerprint" that is important to the useful information contained therein.

Detailed disclosure of the screening assay are published, for example, in Monks et al., *J. Natl. Cancer Inst.*, 83, 757–766 (1991); Skehan et al., *J. Natl. Cancer Inst.*, 82, 1107–1112 (1990); and Boyd and Paull, *Drug Dev. Res.*, 34, 484–488 (1995). The identities, sources, derivation, morphological, and immunocytochemical characteristics, and methods of maintenance of the cell lines comprising the NCI 60 cell-line panel have been described in detail, for example, in Boyd, In: *Cancer: Principles and Practice of Oncology Updates*, DeVita et al., eds., Philadelphia: Lippincott, pp. 1–12 (1989); Stinson et al., Anticancer Res., 12, 1034–1035 (1992).

In the screening assay, each agent is tested over a broad concentration range against every cell line in the panel. All lines are inoculated onto a series of standard 96-well microtitre plates on day zero, followed by a 24 hour incubation in the absence of the test compound. The inoculation densities employed depend upon the particular cell line and its growth characteristics. Inoculation densities used are as published in Monks et al., *J. Natl. Cancer Inst.*, 83, 757–766 (1991); and Boyd and Paull, *Drug Dev. Res.*, 34, 91–109 (1995). Test compounds are evaluated at five 10-fold dilutions. Following a 48-hour incubation with the test compound, the cells are assayed by the sulforhodamine B procedure as described in Skehan et al., *J. Natl. Cancer Inst.*, 82, 1107–1112 (1990); Monks et al., *J. Natl. Cancer Inst.*, 83, 757–766 (1991); and Rubinstein et al., *J. Natl. Cancer Inst.*, 82, 1112–1118 (1990). Optical densities are measured on automated plate readers, followed by computerized data acquisition, processing, storage, and availability for display-and analysis.

Each successful test of a compound generates 60 dose-response curves, which are printed in the NCI screening data report as a series of composites comprising the tumor-type subpanels. Data for any individual cell line(s) failing quality control criteria, or otherwise deficient for any cell line(s) not tested successfully, are eliminated from further analysis and are deleted from the screening report.

The meaning and calculation of response parameters, $GI_{50}$, TGI, and $LC_{50}$, and the construction and use of "mean-graphs" is summarized briefly as follows. The 50% growth inhibition parameter ($GI_{50}$) is the concentration of test drug where $100\times(T-T_0)/(C-T_0)=50=PG$ ("percentage growth"). The optical density of the test well after the 48 hour drug exposure is T; the optical density at time zero is $T_0$; and the control optical density is C. The PG is a T/C-like parameter that can have values from +100 to −100. Whereas the $GI_{50}$ may be viewed as a growth-inhibitory level of effect, the TGI signifies a "total growth inhibition" or cytostatic level of effect. The TGI is the drug concentration where $100\times(T-T_0)/(C-T)=0=PG$. The $LC_{50}$ is the lethal concentration, "net cell killing" or cytotoxicity parameter. It is the concentration where $100\times(T-T_0)/T_0=-50=PG$. The control optical density is not used in the calculation of $LC_{50}$. For a detailed description of the response parameters and the construction and use of mean-graphs, see Boyd et al., In: *Cytotoxic Anticancer Drugs: Models and Concepts for Drug Discovery and Development*, Valeriote et al., eds., Amsterdam: Kluwer Academic Publishers, pp. 11–34 (1992).

A mean-graph is a pattern created by plotting positive and negative values, termed "deltas," generated from a set of $GI_{50}$, TGI, or $LC_{50}$ concentrations obtained for a given compound tested against each cell line in the NCI in vitro screen. The deltas are generated from the $GI_{50}$, TGI, and $LC_{50}$ data by a three-step calculation. For example, the $GI_{50}$ value for each cell line successfully tested against a given compound is converted to its $\log_{10}GI_{50}$ value. The mean panel $\log_{10}GI_{50}$ value is obtained by averaging the individual $\log_{10}GI_{50}$ values. Each $\log_{10}GI_{50}$ value is then subtracted from the panel mean to create the corresponding delta.

To construct the mean-graph, the deltas are plotted horizontally in reference to a vertical line that represents the calculated mean panel $GI_{50}$. The negative deltas are plotted to the right of the mean reference line, thereby proportionately representing cell lines more sensitive than the calculated average. Conversely, the positive deltas are plotted to the left of the reference line to represent the less sensitive cell lines to the given agent. Thus, for example, a bar projecting 3 units to the right of the vertical reference line in a $GI_{50}$ mean-graph indicates that the $GI_{50}$ concentration for that cell line is 1000 times less than the panel-averaged $GI_{50}$ concentration. The TGI and $LC_{50}$ mean-graphs are prepared and interpreted similarly.

Three additional numbers are printed at the base of each of the three respective mean-graphs. These numbers are the MG-MID, the Delta, and the Range. The MG-MID is the calculated mean panel $GI_{50}$, TGI, and $LC_{50}$. The Delta is the number of log10 units by which the delta of the most sensitive line(s) of the panel differ(s) from the delta(s) of the least sensitive line(s).

Representative mean-graphs for several of the compounds of the present invention which demonstrate the results of the screen are depicted in FIGS. 1a–e. To screen the compounds, stock solutions of the compounds were prepared initially in dimethylsulfoxide at 400× the desired final highest test concentrations and stored at −70° C. until use. The final highest test concentrations studied in this example varied between $10^{-4}$ and $10^{-6}$ molar. At the time of screening, an aliquot of the thawed stock was diluted with complete medium containing 50 µg/ml gentamycin to give a concentration of 2× the desired final highest test concentration. An additional four, 10-fold serial dilutions were then made to provide a total of five concentrations, spanning a 4-log10 concentration range. One hundred µL aliquots of these intermediate dilutions were immediately added to the appropriate microtitre wells, each already containing the appropriate numbers and types of cells in 100 µL of culture medium, resulting in the desired five final concentrations.

The 60 cell lines used, and the respective inoculation densities, were as described in Boyd and Paull, *Drug Dev. Res.*, 34, 91–109 (1995); Monks et al., *J. Natl. Cancer Inst.*, 83, 757–766 (1991). Following the compound additions, the plates were incubated for 48 hours at 37° C. under a 5% $CO_2$/air atmosphere and 100% humidity. Then, adherent cells (all lines except the leukemia) were fixed in situ by gentle addition of cold trichloroacetic acid (50 µL of 50% w/v) and incubated for 60 minutes at 4° C. Supernatants were discarded, and plates were washed 5 times with deionized water and air dried. Sulforhodamine B solution was added to each plate, followed by further incubation for 10 minutes at room temperature. Excess unbound dye was then removed by washing 5 times with 1% acetic acid, followed by air drying. The bound stain in each well was solubilized by addition of 100 µL of 10 mmol/L unbuffered Tris base; this was followed by a determination of optical densities on an automated plate reader. For suspension cell cultures (the leukemias), the method was the same except that at the end of the drug incubation period the settled cells were fixed in situ to the bottoms of the microtitre wells by gentle addition of 50 µL of 80% trichloracetic acid. Appropriate control wells were included in the test plate format to allow subtraction of background optical densities, drug-blank corrections, and a determination of cell densities at time 0 (the time at which compounds were added).

Figure 1A:
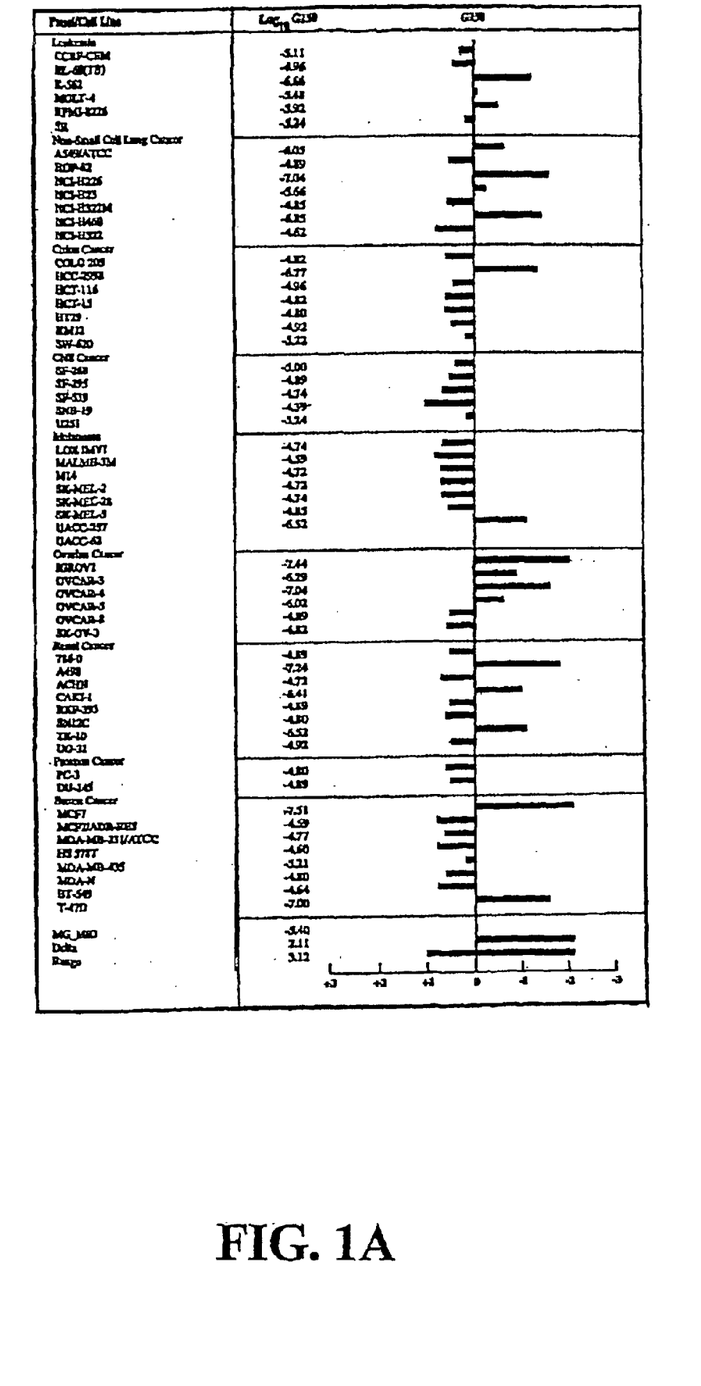
FIG. 1A illustrates the $GI_{50}$-based mean-graph "fingerprint" of 5-amino-6,8-difluoro-2-[3-fluoro-4-[(L-lysyl)amino]phenyl]-7-methyl-4H-1-benzopyran-4-one, trihydrobromide in the NCI 60 cell-line screen.
Figure 1B:
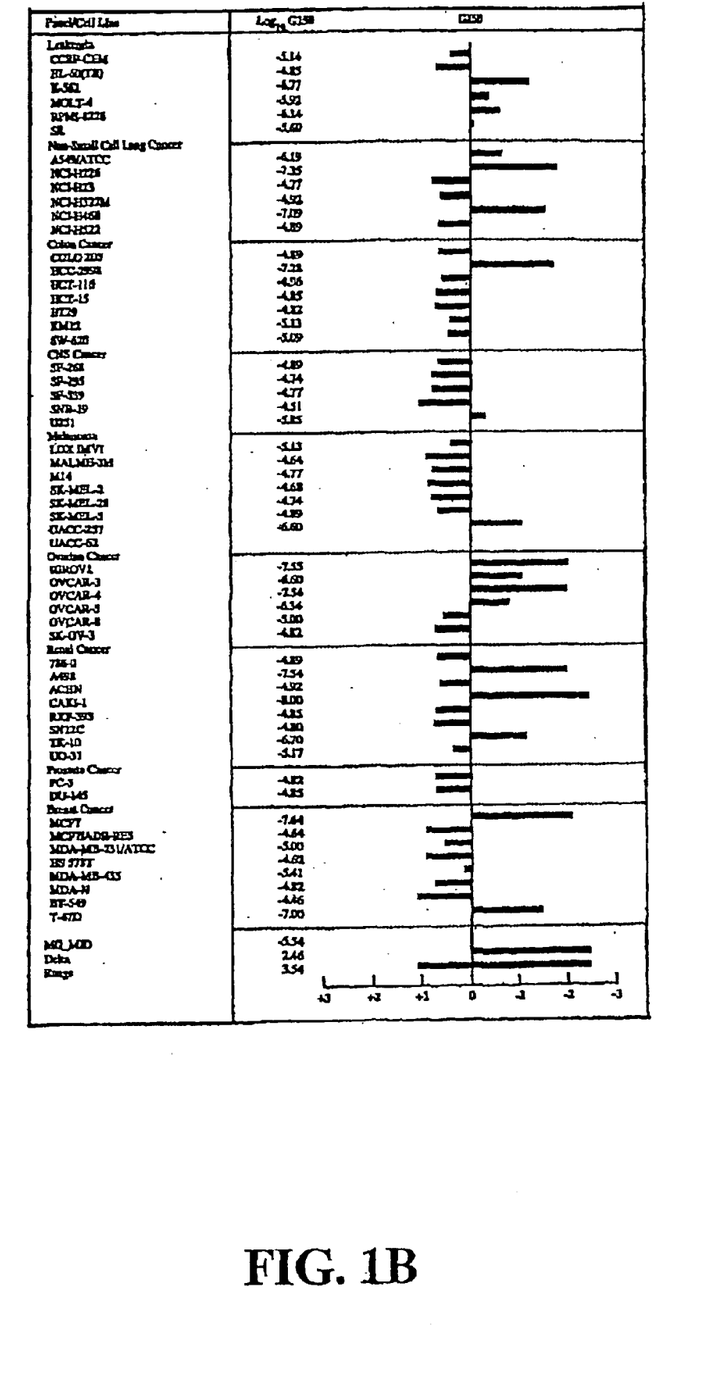
FIG. 1B illustrates the $GI_{50}$-based mean-graph "fingerprint" of 5-amino-6,8-difluoro-2-[3-fluoro-4-[(L-lysyl)amino]phenyl]-7-methyl-4H-1-benzopyran-4-one, dimethanesulfonate in the NCI 60 cell-line screen.
Figure 1C:
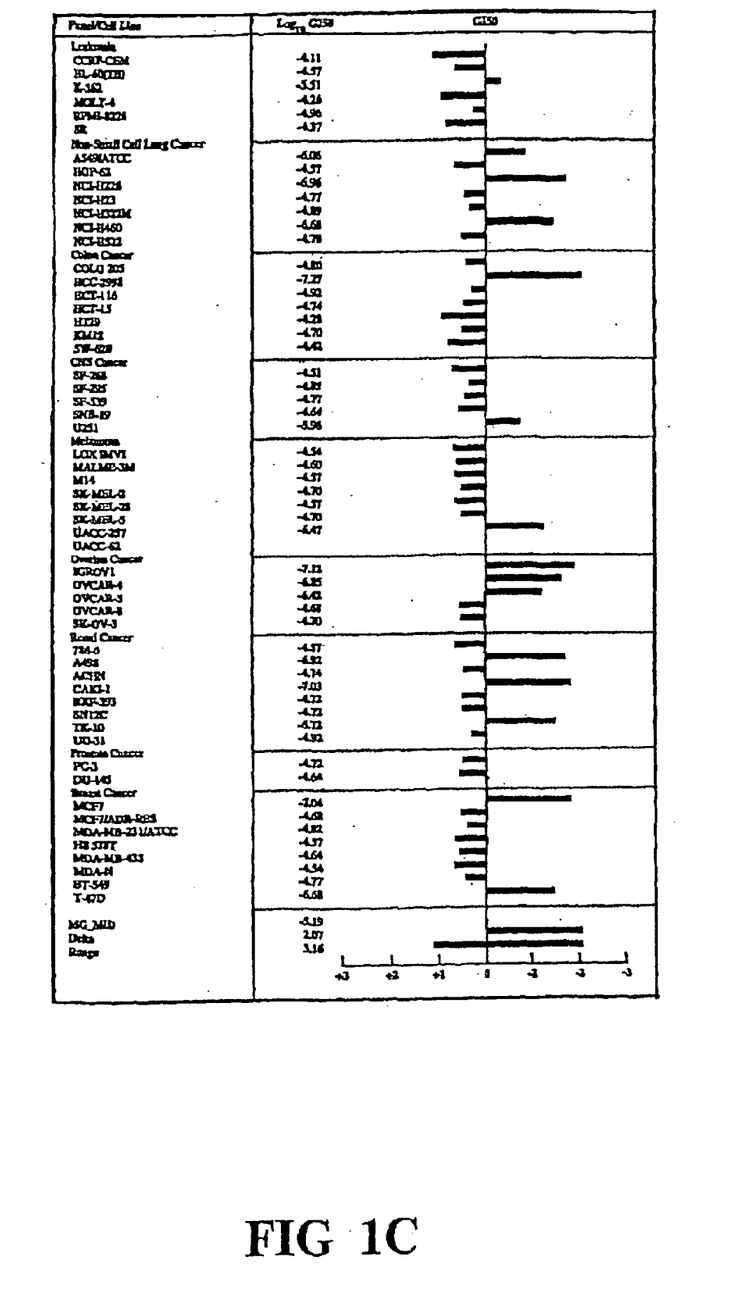
FIG. 1C illustrates the $GI_{50}$-based mean-graph "fingerprint" of 5-amino-2-[4-[[2-amino-5-guanidinopentanoyl]amino]-3-fluorophenyl]-6,8-difluoro-7-methyl-4H-1-benzopyran-4-one, trihydrobromide in the NCI 60 cell-line screen.
Figure 1D:
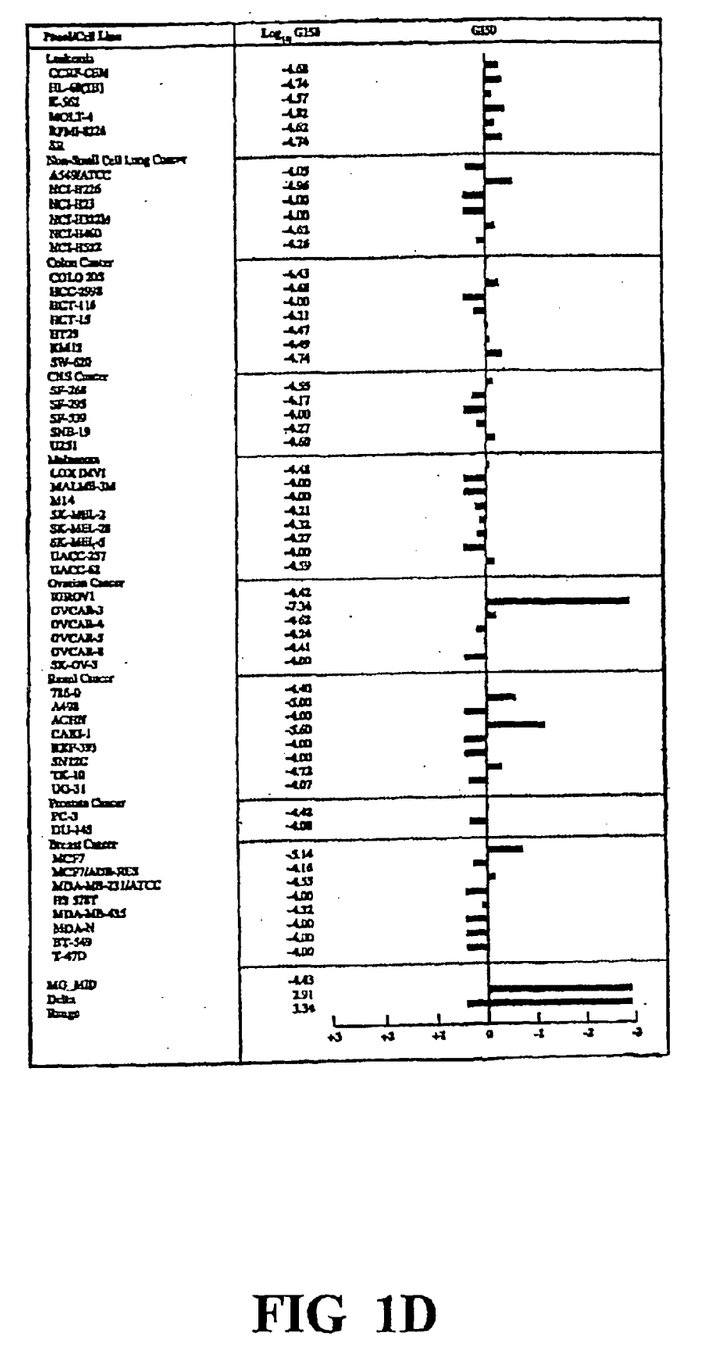
FIG. 1D illustrates the $GI_{50}$-based mean-graph "fingerprint" of 5-amino-6,8-difluoro-7-methyl-2-[4-(dimethylamino)acetamido-3-fluorophenyl]-4H-1-benzopyran-4-one in the NCI 60 cell-line screen.
Figure 1E:
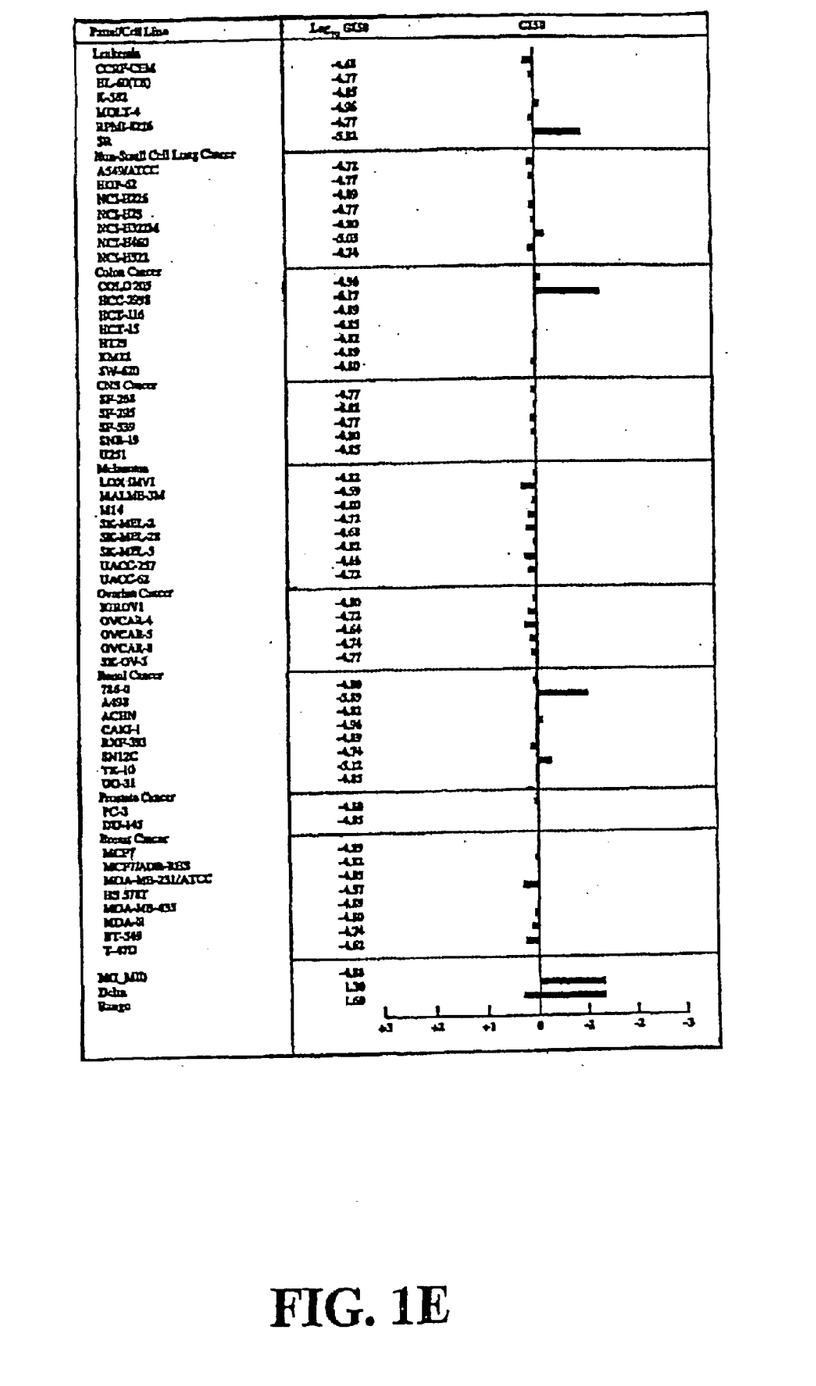
FIG. 1E illustrates the $GI_{50}$-based mean-graph "fingerprint" of 6,8-difluoro-7-methyl-5-(dimethylamino)acetamido-2-[4-(dimethylamino)acetamido-3-fluorophenyl]-4H-1-benzopyran-4-one in the NCI 60 cell-line screen.

As is evident from FIG. 1B, for example, compound 1a demonstrated tumor growth-inhibiting activity against several human cancer cell lines, particularly against breast (e.g., MCF7), ovarian (e.g., OVCAR-5), renal (e.g., CAKI-1), and colon (e.g., SW-620) cancer cell lines.

EXAMPLE 17

This Example illustrates the desirable solubility characteristics of the aminoflavone compounds of the present invention. In Table 2 below, the water solubility of compounds 1a–d of Table 1 are set forth at different pH with a citrate or phosphate buffer, as indicated. Solubility was determined visually at a fixed concentration of 5 mg/mL.

TABLE 2

Visual Solubility Evaluation of Aminoflavone Compounds of the Present Invention

| Cpd | pH 3* | pH 5* | pH 7** |
|---|---|---|---|
| 1a | S | NFS | NFS |
| 1b | S | NFS | NFS |
| 1c | NFS | NFS | NFS |
| 1d | S | S | NFS |

*citrate buffer;
**phosphate buffer
S = fully soluble;
NFS = Not Fully Soluble

The data in Table 2 demonstrate that compounds 1a, b, and d were fully soluble at pH 3. Compound 1d was also fully soluble at pH 5. Although at higher pH levels, most of the compounds demonstrated a reduced solubility, they remain more water soluble than some other 5,4'-diaminoflavones, such as 5,4'-diamino-6,8,3'-trifluoroflavone. See Akama et al., *J. Med. Chem.*, 41, 2056–2067 (1998) (noting the water solubility of 5,4'-diamino-6,8,3'-trifluoroflavone to be less than 0.2 µg/mL).

EXAMPLE 18

This example illustrates the preparation of 7-(acetoxymethyl)-5-amino-2-[4-(chloroacetamido)-3-fluorophenyl]-6,8-difluoro-4H-1-benzopyran-4-one.

To a solution of 7-(acetoxymethyl)-5-amino-2-(4-amino-3-fluorophenyl)-6,8-difluoro-4H-1-benzopyran-4-one (3.20 g) in dimethylformamide (60 mL) were added monochloroacetic acid (1.60 g) and 1-(3-dimethylaminopropyl)-3-ethylcarbodiimide hydrochloride (3.23 g), and the mixture was stirred at room temperature for 22 hours. Water was added thereto, and the crystals precipitated were collected by filtration to afford the final product.

$C_{20}H_{14}{}^{35}ClF_3N_2O_5$=454. Found: 455 $(M+H)^+$.

EXAMPLE 19

This example illustrates the preparation of 2-[4-(allyloxycarbonyl)amino-3-fluorophenyl]-7-[(allyloxycarbonyl)oxy]methyl-5-amino-6,8-difluoro-4H-1-benzopyran-4-one.

To a solution of 5-amino-2-(4-amino-3-fluorophenyl)-6,8-difluoro-7-(hydroxymethyl)-4H-1-benzopyran-4-one (1.01 g) in pyridine (30 mL) was added allyl chloroformate (3.2 mL) at 0° C., and the mixture was stirred at room temperature for 3 hours. Water was added thereto and the crystals precipitated were collected by filtration. Purification by silica gel column chromatography (chloroform) gave the final product.

$C_{24}H_{19}F_3N_2O_7$=504. Found: 505 $(M+H)^+$.

EXAMPLE 20

This example illustrates the preparation of 2-[4-(allyloxycarbonyl)amino-3-fluorophenyl]-7-[(allyloxycarbonyl)oxy]methyl-5-(chloroacetamido)-6,8-difluoro-4H-1-benzopyran-4-one.

To a solution of 2-[4-(allyloxycarbonyl)amino-3-fluorophenyl)-7-[(allyloxycarbonyl)oxy]methyl-5-amino-6,8-difluoro-4H-1-benzopyran-4-one (2.02 g) in dimethylformamide (40 mL) were added monochloroacetic acid (1.90 g) and 1-(3-dimethylaminopropyl)-3-ethylcarbodiimide hydrochloride (3.84 g) and the mixture was stirred at room temperature for 8 hours. Water was added thereto, and the crystals precipitated were collected by filtration. Purification by silica gel column chromatography (9.1 chloroform/ethyl acetate) gave the final product.

$C_{26}H_{20}{}^{35}ClF_3N_2O_8$=580. Found: 581 (M+H)$^+$.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. An aminoflavone having the following formula:

wherein each of $R^1$ and $R^2$ is H, COCH$_2$—R$^7$, wherein R$^7$ is amino, branched or straight-chain alkylamino, dialkylamino, or alkyl- or dialkylaminoalkyl, or an α-amino acid residue, provided that at least one of $R^1$ or $R^2$ is other than H, and wherein R$^3$ is H, branched or straight-chain alkyl, hydroxyalkyl, alkanoyloxyalkyl, alkanoyloxy, alkoxy, or alkoxyalkyl, or a pharmaceutically acceptable salt thereof.

2. The aminoflavone of claim 1, wherein when each of $R^1$ or $R^2$ is an α-amino acid residue, the stereochemistry of $R^1$ and $R^2$ is L.

3. The aminoflavone of claim 1, wherein the compound is selected from the group consisting of 5-amino-6,8-difluoro-2-[3-fluoro-4-[(L-lysyl)amino]phenyl]-7-methyl-4H-1-benzopyran-4-one, 5-amino-2-[4-[[2-amino-5-guanidinopentanoyl]amino]-3-fluorophenyl]-6,8-difluoro-7-methyl-4H-1-benzopyran-4-one, 6,8-difluoro-7-methyl-5-(dimethylamino)acetamido-2-[4-(dimethylamino)acetamido-3-fluorophenyl]-4H-1-benzopyran-4-one, and 5-amino-6,8-difluoro-7-methyl-2-(4-(dimethylamino)acetamido-3-fluorophenyl]-4H-1-benzopyran-4-one.

4. A composition comprising an aminoflavone having the following formula:

wherein each of $R^1$ and $R^2$ is H, COCH$_2$—R$^7$, wherein R$^7$ is amino, branched or straight-chain alkylamino, dialkylamino, or alkyl- or dialkylaminoalkyl, or an α-amino acid residue, provided that at least one of $R^1$ or $R^2$ is other than H, and wherein R$^3$ is H, branched or straight-chain alkyl, hydroxyalkyl, alkanoyloxyalkyl, alkanoyloxy, alkoxy, or alkoxyalkyl, or a pharmaceutically acceptable salt thereof, and a pharmaceutically acceptable carrier.

5. The composition of claim 4, wherein the aminoflavone is selected from the group consisting of 5-amino-6,8-difluoro-2-[3-fluoro-4-[(L-lysyl)amino]phenyl]-7-methyl-4H-1-benzopyran-4-one, 5-amino-2-[4-[[2-amino-5-guanidinopentanoyl]amino]-3-fluorophenyl]-6,8-difluoro-7-methyl-4H-1-benzopyran-4-one, 6,8-difluoro-7-methyl-5-(dimethylamino)acetamido-2-[4-(dimethylamino)acetamido-3-fluorophenyl]-4H-1-benzopyran-4-one, and 5-amino-6,8-difluoro-7-methyl-2-[4-(dimethylamino)acetamido-3-fluorophenyl]-4H-1-benzopyran-4-one.

6. The composition of claim 4 wherein the composition further comprises at least one other anticancer agent.

7. A method of inhibiting the growth of a tumor in a host comprising administering to said host a tumor growth-inhibiting amount of an aminoflavone having the following general formula:

wherein each of $R^1$ and $R^2$ is H, COCH$_2$—R$^7$, wherein R$^7$ is amino, branched or straight-chain alkylamino, dialkylamino, or alkyl- or dialkylaminoalkyl, or an α-amino acid residue, provided that at least one of $R^1$ or $R^2$ is other than H, and wherein R$^3$ is H, branched or straight-chain alkyl, hydroxyalkyl, alkanoyloxyalkyl, alkanoyloxy, alkoxy, or alkoxyalkyl, or a pharmaceutically acceptable salt thereof.

8. The method of claim 7, comprising administering a composition comprising the aminoflavone and a pharmaceutically acceptable carrier.

9. The method of claim 7, wherein a tumor growth-inhibiting amount of at least one other anticancer agent is administered to said host.

10. The method of claim 7, wherein said tumor is selected from the group consisting of breast, ovarian, and kidney tumors.

11. The method of claim 7, wherein the aminoflavone is selected from the group consisting of 5-amino-6,8-difluoro-2-[3-fluoro-4-[(L-lysyl)amino]phenyl]-7-methyl-4H-1-benzopyran-4-one, 5-amino-2-[4-[[2-amino-5-guanidinopentanoyl]amino]-3-fluorophenyl]-6,8-difluoro-7-methyl-4H-1-benzopyran-4-one, 6,8-difluoro-7-methyl-5-(dimethylamino)acetamido-2-[4-(dimethylamino)acetamido-3-fluorophenyl]-4H-1-benzopyran-4-one, and 5-amino-6,8-difluoro-7-methyl-2-[4-(dimethylamino)acetamido-3-fluorophenyl]-4H-1-benzopyran-4-one.

12. The composition of claim 5, wherein the composition further comprises at least one other anticancer agent.

13. The method of claim 8, wherein a tumor growth-inhibiting amount of at least one other anticancer agent is administered to said host.

14. The method of claim 8, wherein said tumor is selected from the group consisting of breast, ovarian, and kidney tumors.

15. The method of claim 8, wherein the aminoflavone is selected from the group consisting of 5-amino-6,8-difluoro-2-[3-fluoro-4-[(L-lysyl)amino]phenyl]-7-methyl-4H-1-benzopyran-4-one, 5-amino-2-[4-[[2-amino-5-guanidinopentanoyl]amino]-3-fluorophenyl]-6,8-difluoro-7-methyl-4H-1-benzopyran-4-one, 6,8-difluoro-7-methyl-5-(dimethylamino)acetamido-2-[4-(dimethylamino)acetamido-3-fluorophenyl]-4H-1-benzopyran-4-one, and 5-amino-6,8-difluoro-7-methyl-2-[4-(dimethylamino)acetamido-3-fluorophenyl]-4H-1-benzopyran-4-one.

\* \* \* \* \*